United States Patent
Mohn et al.

(10) Patent No.: US 9,120,014 B2
(45) Date of Patent: *Sep. 1, 2015

(54) SYSTEM AND METHOD FOR GATHERING AND ANALYZING OBJECTIVE MOTION DATA

(71) Applicant: HOME BOX OFFICE, INC., New York, NY (US)

(72) Inventors: Timothy Mohn, Los Angeles, CA (US); Michael Gabriel, Old Greenwich, CT (US); Jamyn Edis, New York, NY (US); Thomas Igoe, New York, NY (US); Despina Papadopoulous, New York, NY (US); Zachary Eveland, Brooklyn, NY (US)

(73) Assignee: Home Box Office, Inc., New York, NY (US)

( * ) Notice: Subject to any disclaimer, the term of this patent is extended or adjusted under 35 U.S.C. 154(b) by 6 days.

This patent is subject to a terminal disclaimer.

(21) Appl. No.: 14/134,092

(22) Filed: Dec. 19, 2013

(65) Prior Publication Data

US 2014/0106833 A1    Apr. 17, 2014

Related U.S. Application Data

(63) Continuation of application No. 12/502,726, filed on Jul. 14, 2009, now Pat. No. 8,622,795.

(60) Provisional application No. 61/119,915, filed on Dec. 4, 2008.

(51) Int. Cl.
*A63B 69/00* (2006.01)
*A63F 13/20* (2014.01)

(Continued)

(52) U.S. Cl.
CPC .............. *A63F 13/06* (2013.01); *A63B 24/0006* (2013.01); *A63B 69/20* (2013.01);

(Continued)

(58) Field of Classification Search
CPC ........................... A63F 13/06; A63B 24/0006
USPC .......... 463/1–6, 40–42; 702/41, 49, 141, 149; 73/768; 324/71.1; 473/450
See application file for complete search history.

(56) References Cited

U.S. PATENT DOCUMENTS 2,767,920 A    9/1954   Roberson
4,534,557 A    8/1985   Bigelow et al.

(Continued)

OTHER PUBLICATIONS

Atha et al., The damaging punch, British Medical Journal, 1985, pp. 1756-1757. vol. 291.

(Continued)

*Primary Examiner* — Ronald Laneau
*Assistant Examiner* — Ross Williams
(74) *Attorney, Agent, or Firm* — Eric L. Sophir; Dentons US LLP

(57) ABSTRACT

The systems and methods described herein attempt to provide data capture and analysis in a non-intrusive fashion. The captured data can be analyzed for qualitative conclusions regarding an object's actions. For example, a system for analyzing activity of an athlete to permit qualitative assessments of that activity comprises a first processor to receive activity-related data from sensors on the athlete. A first database stores the activity-related data. A second database contains pre-identified motion rules. A second processor compares the received activity-related data to the pre-identified motion rules, wherein the second processor identifies a pre-identified motion from the pre-identified motion rules that corresponds to the received activity-related data. A memory stores the identified pre-selected motion.

18 Claims, 13 Drawing Sheets

(51) Int. Cl.
*A63B 24/00* (2006.01)
*A63B 69/20* (2006.01)
*A63B 71/10* (2006.01)
*A63B 71/14* (2006.01)
*A63B 71/06* (2006.01)

(52) U.S. Cl.
CPC ............ *A63B 71/10* (2013.01); *A63B 71/145* (2013.01); *A63B 2024/0012* (2013.01); *A63B 2071/0636* (2013.01); *A63B 2220/13* (2013.01); *A63B 2220/40* (2013.01); *A63B 2220/51* (2013.01); *A63B 2220/53* (2013.01); *A63B 2220/803* (2013.01); *A63B 2220/806* (2013.01); *A63B 2225/20* (2013.01); *A63B 2225/50* (2013.01); *A63B 2230/50* (2013.01); *A63B 2243/007* (2013.01); *A63B 2243/0025* (2013.01); *A63B 2244/102* (2013.01)

(56) References Cited

U.S. PATENT DOCUMENTS

| | | | |
|---|---|---|---|
| 4,763,284 | A | 8/1988 | Carlin |
| 4,883,271 | A | 11/1989 | French |
| 5,184,831 | A | 2/1993 | Garner |
| 5,279,163 | A | 1/1994 | D'Antonio et al. |
| 5,502,841 | A | 4/1996 | Stanford |
| 5,553,860 | A | 9/1996 | Zelikovich |
| 5,573,406 | A | 11/1996 | Fowler |
| 5,723,786 | A | 3/1998 | Klapman |
| 6,567,536 | B2 | 5/2003 | McNitt et al. |
| 6,611,782 | B1 | 8/2003 | Wooster et al. |
| 6,659,350 | B2 | 12/2003 | Schwartz et al. |
| 6,710,713 | B1 | 3/2004 | Russo |
| 6,925,851 | B2 | 8/2005 | Reinbold et al. |
| 6,975,230 | B1 | 12/2005 | Brilman |
| 7,017,808 | B2 | 3/2006 | Holzer |
| 7,264,554 | B2 | 9/2007 | Bentley |
| 7,308,818 | B2 | 12/2007 | Considine et al. |
| 7,328,612 | B2 | 2/2008 | Jamsen et al. |
| 7,384,380 | B2 | 6/2008 | Reinbold et al. |
| 7,421,369 | B2 | 9/2008 | Clarkson |
| 7,424,388 | B2 | 9/2008 | Sato |
| 7,503,878 | B1 | 3/2009 | Amsbury et al. |
| 7,552,031 | B2 | 6/2009 | Vock et al. |
| 7,689,378 | B2 | 3/2010 | Kolen |
| 7,715,982 | B2 | 5/2010 | Grenfell et al. |
| 7,736,242 | B2 | 6/2010 | Stites et al. |
| 7,811,333 | B2 | 10/2010 | Jonsson |
| 7,980,998 | B2 | 7/2011 | Shemesh et al. |
| 7,980,999 | B2 | 7/2011 | Kawaguchi et al. |
| 8,070,655 | B1 | 12/2011 | Napolitano et al. |
| 8,075,499 | B2 | 12/2011 | Nathan et al. |
| 2002/0092347 | A1 | 7/2002 | Niekerk et al. |
| 2002/0165758 | A1 | 11/2002 | Hind et al. |
| 2003/0181290 | A1 | 9/2003 | Black |
| 2004/0074966 | A1 | 4/2004 | Holzer |
| 2004/0092311 | A1 | 5/2004 | Weston et al. |
| 2004/0225236 | A1 | 11/2004 | Wheeler et al. |
| 2005/0250625 | A1 | 11/2005 | Reinbold et al. |
| 2005/0266967 | A1 | 12/2005 | Considine et al. |
| 2006/0022833 | A1 | 2/2006 | Ferguson et al. |
| 2006/0047447 | A1 | 3/2006 | Brady et al. |
| 2007/0184908 | A1 | 8/2007 | Hansen |
| 2007/0191141 | A1 | 8/2007 | Weber |
| 2007/0213126 | A1 | 9/2007 | Deutsch et al. |
| 2008/0094472 | A1 | 4/2008 | Ayer et al. |
| 2008/0232786 | A1 | 9/2008 | Wilharm |
| 2009/0029754 | A1 | 1/2009 | Slocum et al. |
| 2009/0280921 | A1 | 11/2009 | Rankin |
| 2010/0026809 | A1 | 2/2010 | Curry |
| 2010/0041498 | A1 | 2/2010 | Adams |
| 2010/0075806 | A1 | 3/2010 | Montgomery |
| 2010/0076692 | A1 | 3/2010 | Vock et al. |
| 2010/0106044 | A1 | 4/2010 | Linderman |
| 2010/0194879 | A1 | 8/2010 | Pasveer et al. |
| 2010/0204615 | A1 | 8/2010 | Kyle et al. |
| 2010/0234699 | A1 | 9/2010 | Lanfermann et al. |
| 2010/0261146 | A1 | 10/2010 | Kim |
| 2010/0323805 | A1 | 12/2010 | Kamino |
| 2011/0118621 | A1 | 5/2011 | Chu |
| 2011/0140931 | A1 | 6/2011 | Geurts et al. |
| 2011/0144543 | A1 | 6/2011 | Tsuzuki et al. |
| 2011/0156868 | A1 | 6/2011 | Hoeflinger et al. |
| 2011/0159939 | A1 | 6/2011 | Lin et al. |

OTHER PUBLICATIONS

Cesari et al., Coupling between punch efficacy and body stability for elite karate, Jounal of Science and Medicine in Sport, 2008, pp. 353-356, vol. 11.

Pierce et al., Direct Measurement of Punch Force During Six Professional Boxing Matches, Journal of Quantitative Analysis in Sports, 2006, pp. 1-17, vol. 2, No. 2, Issue 3, 19 pages.

Smith et al., Development of a boxing dynamometer and its punch force discrimination efficacy, Journal of Sports Sciences, 2000, pp. 445-450, vol. 18.

Vos et al., Physiology Velocity Forces of Some Karate Arm-movements, Nature, 1966, vol. 211.

Warnick et al., Specification of Variables Predictive of Victories in the Sport of Boxing. Perceptual Motor Skills, 2007, pp. 153-158, vol. 105.

Warnick et al., Specification of Variables Predictive of Victories in the Sport of Boxing. Perceptual Motor Skills: II. Further Characterization of Previous Success, Feb. 2009.

Whiting et al., Kinematic analysis of human upper extremity movements in boxing, American Journal of Sports Medicine, 1988, pp. 130-136. vol. 16, No. 2.

Engineers Prove That Boxer, 'Hitman' Hatton, Packs A Mighty Punch, 2007, ScienceDaily, downloaded from http://www.sciencedaily.com/releases/2007/06/070622090701.htm, 3 pages.

Bagreev et al., Some peculiarities in measurement of dynamic processes in biomechanics, Biomechanics VII-A, International Series on Biomechanics, 1981, pp. 511-513, vol. 3A, University Park Press, Baltimore (7 pages).

Karpilowski et al., A Versatile Boxing Simulator. Biology of Sport, 1994, pp. 133-139, vol. 11, No. 2 (8 pages).

Sherman et al., Correlation between punch dynamics and risk of injury, Engineering of Sport 5, 2004, pp. 110-116, vol. 2, UC Davis, CA (17 pages).

Patridge et al., "A Wireless-Sensor Scoring and Training System for Combative Sports," Proceedings of SPIE: Smart Structures, Devices, and Systems II, vol. 5649, 7 pages.

Mihalik et al., "Characteristics of head impacts sustained by youth ice hockey players," Proc. ImechE: J. Sports Engineering and Technology, vol. 222, Part P, 8 pages (2008).

Komi et al., "Measurement and analysis of grip force during a golf shot," Proc. ImechE: J. Sports Engineering and Technology, vol. 222, Part P, 14 pages, (2008).

Walsh et al., "The Smart Helmet: A Practical Demonstration of Smart Environments in Sports," Advances in Pervasive Computing 2006, Adjunct Proceedings of Pervasive 2006, Dublin May 7-10, 6 pages.

Papakostas et al., "A Large Area Force Sensor for Smart Skin Applications," Sensors. 2002. Proceedings of IEEE, 5 pages.

Wattanamonggkhol et al., "A Method of Glove Tracking for Amateur Boxing Refereeing," IEEE International Symposium on Communications and Information, Technology, 2005, ISCIT 2005, 4 pages.

International Search Report and Written Opinion dated Oct. 9, 2009 issued in corresponding International Application No. PCT/US2009/054634, 9 pages.

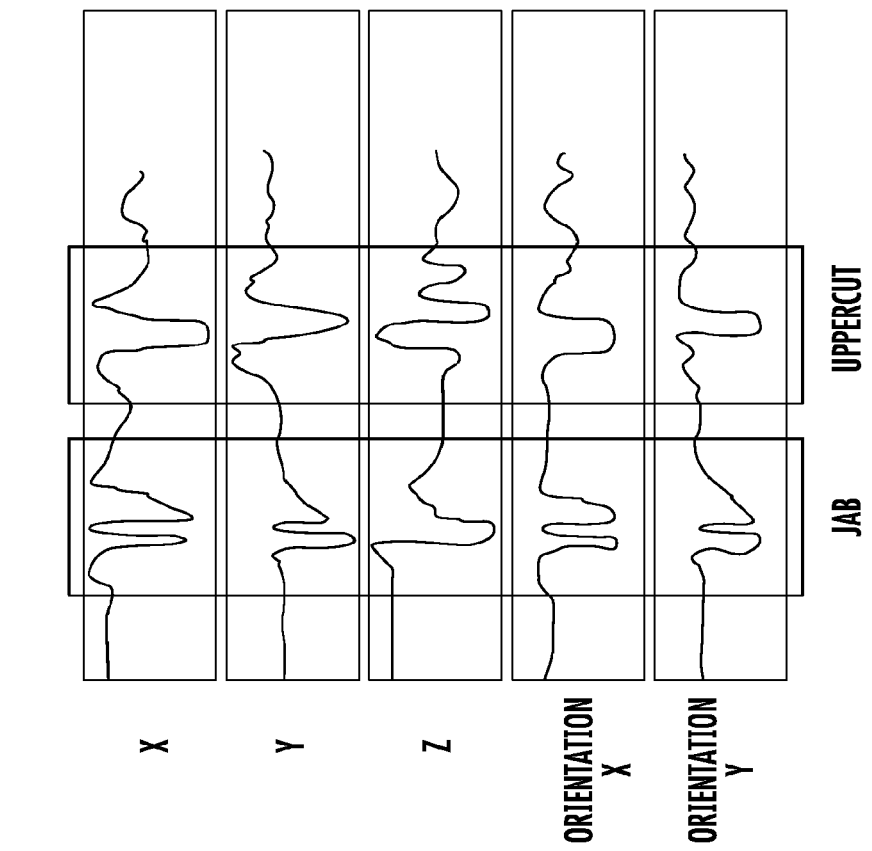
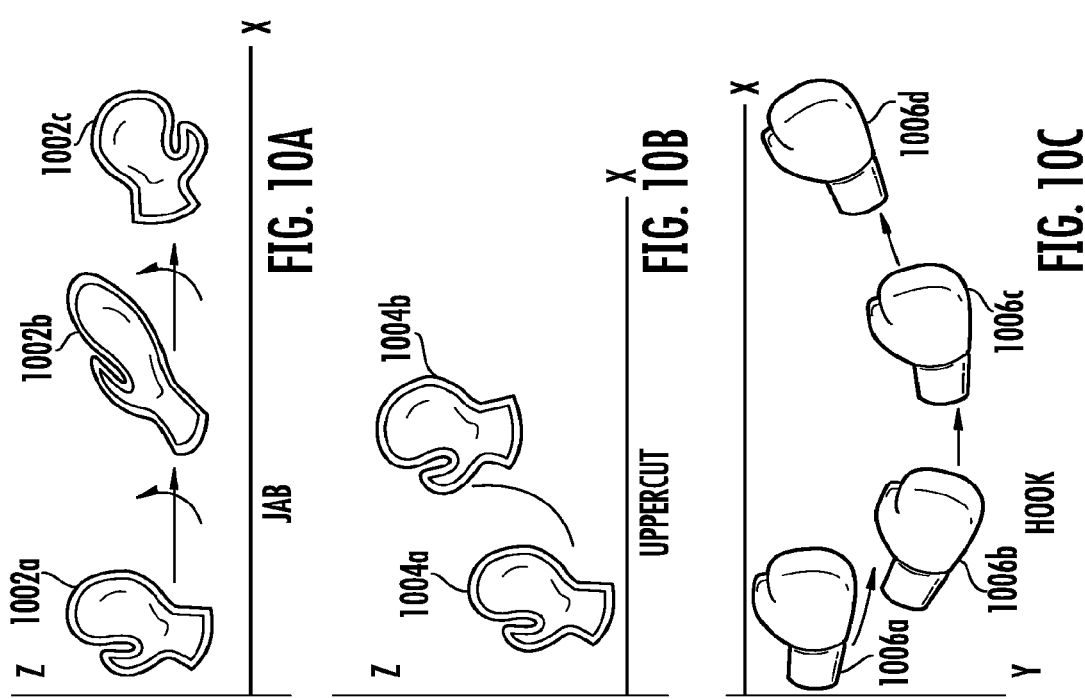
FIG. 10A
FIG. 10B
FIG. 10C
FIG. 10D

SYSTEM AND METHOD FOR GATHERING AND ANALYZING OBJECTIVE MOTION DATA

CROSS-REFERENCE TO RELATED APPLICATIONS

This application is a continuation of U.S. patent application Ser. No. 12/502,726, filed Jul. 14, 2009, entitled "SYSTEM AND METHOD FOR GATHERING AND ANALYZING OBJECTIVE MOTION DATA," which claims priority to U.S. Provisional Patent Application No. 61/119,915, filed Dec. 4, 2008, entitled, "SYSTEM AND METHOD FOR GATHERING AND ANALYZING OBJECTIVE MOTION DATA," which are herein incorporated by reference in their entirety.

BACKGROUND

1. Field of the Invention

The invention relates generally to the field of analyzing motion data for translation to qualitative assessment, and more particularly, to systems and methods for the analysis and display of qualitative outcomes regarding object data in sports entertainment.

2. Description of the Related Art

Many currently available data capture and analysis devices for athletes are intrusive to the athlete's performance. As a result, the devices may not be effectively used in an analysis during an event. In another scenario, the athlete may refuse to incorporate the device into his equipment or attire. A professional boxer, for example, wears footwear, boxer shorts, and boxing gloves during a boxing bout. Some amateur boxers can wear head gear and a vest, but a professional boxer does not. In another example, a soccer player wears footwear, shin guards, shorts, and a shirt. An athlete's uniform is designed for maximum mobility and protection, and should not impede the performance of the athlete. Thus, there is a need for a system and a method for data capture and analysis that does not interfere with an athlete's actions and abides by the rules of the sport.

SUMMARY

The systems and methods described herein attempt to provide data capture and analysis in a non-intrusive fashion. The captured data can be analyzed for qualitative conclusions regarding an object's actions.

In one embodiment, a computer-implemented method analyzes activity of an athlete to permit qualitative assessments of that activity using a processor. The method comprises receiving activity-related data from sensors on the athlete. A database stores the activity-related data. The processor compares the received activity-related data against a set of pre-identified discrete outcomes. The processor identifies by the processor one of the pre-identified outcomes as corresponding to the received activity-related data based on the comparison of the received activity-related data against the set of pre-identified outcomes. The identified pre-identified outcome is displayed.

In another embodiment, a system for analyzing activity of an athlete to permit qualitative assessments of that activity comprises a first processor to receive activity-related data from at least one sensor on the athlete. The at least one sensor has a first three-axis accelerometer coupled to the first processor and a first gyroscope coupled to the first processor. A first database stores the activity-related data from the at least one sensor. A second database contains pre-identified motion rules. A transmitter couples to the first processor to transmit the activity-related data to a second processor. A receiver couples to the second processor to receive the activity related data from the transmitter. The second processor compares the received activity-related data to the pre-identified motion rules, wherein the second processor identifies a pre-identified motion from the pre-identified motion rules that corresponds to the received activity-related data. A memory stores the identified pre-selected motion.

In another embodiment, a method analyzes hand activity of a boxer with an accelerometer and a gyroscope disposed on a hand of the boxer using a computer having a memory to permit qualitative assessments of the activity. The method comprises receiving by a computer hand activity-related accelerometer data from the accelerometer disposed on the hand of the boxer. A computer receives hand activity-related gyroscope data from the gyroscope disposed on the hand of the boxer. The memory stores the hand activity-related accelerometer and the hand activity-related gyroscope data. The computer detects a hand event and if a hand motion is detected, compares the received hand activity-related accelerometer data and hand activity-related gyroscope data against a motion profile. The computer identifies a hand motion corresponding to the received hand activity-related accelerometer and gyroscope data based on the comparison of the received hand activity-related accelerometer and gyroscope data against the motion profile.

In another embodiment, a computer program product has a computer usable medium having computer readable program code embodied therein for analyzing hand activity of a boxer with an accelerometer and a gyroscope disposed on a hand of the boxer. The computer readable program code in the computer program product has computer readable program code for receiving hand activity-related accelerometer data from the accelerometer disposed on the hand of the boxer. The computer readable program code has code for receiving hand activity-related gyroscope data from the gyroscope disposed on the hand of the boxer. The computer readable program code has code for storing the hand activity-related accelerometer and the hand activity-related gyroscope data in the memory. Additionally, there is computer readable program code for detecting a hand event. The computer readable program code has code for comparing the received hand activity-related accelerometer data and hand activity-related gyroscope data against a motion profile if the hand event is detected. The computer readable program code has code for identifying a hand motion corresponding to the received hand activity-related accelerometer and gyroscope data based on the comparison of the received hand activity-related accelerometer and gyroscope data against the motion profile.

In another embodiment, a computer program product has a computer usable medium that has computer readable program code embodied therein for analyzing activity of an athlete to permit qualitative assessments of that activity. The computer program product has code for receiving activity-related data from sensors on the athlete. The computer readable program code has code storing the activity-related data in a database. The computer readable program code has code for comparing by the received activity-related data against a set of pre-identified discrete outcomes. The computer readable program code has code for identifying by the processor one of the pre-identified outcomes as corresponding to the received activity-related data based on the comparison of the received activity-related data against the set of pre-identified outcomes. The computer readable program code for displaying the identified pre-identified outcome.

In another embodiment, a system analyzes punch activity of a boxer with an accelerometer and a gyroscope disposed on a hand of the boxer to permit qualitative assessments of the activity. The system has means for receiving hand activity-related accelerometer data from the accelerometer disposed on the hand of the boxer, a means for receiving hand activity-related gyroscope data from the gyroscope disposed on the hand of the boxer, a means for storing the hand activity-related accelerometer and the hand activity-related gyroscope data, a means for detecting a hand event, a means for comparing the received hand activity-related accelerometer data and hand activity-related gyroscope data against a motion profile if the hand event is detected, and a means for identifying a hand motion corresponding to the received hand activity-related accelerometer and gyroscope data based on the comparison of the received hand activity-related accelerometer and gyroscope data against the motion profile.

In another embodiment, a computer-implemented method displays qualitative hand assessment data of a boxer having an accelerometer and a gyroscope disposed on a hand of the boxer. The method has a computer that receives a real-time video data of the boxer. The computer receives data from a visualization engine, wherein the data comprises a real-time hand analysis data, and wherein the real-time hand analysis data comprises data identified by the analysis engine as one of a pre-identified outcome stored in a database corresponding to the data from the accelerometer and the gyroscope. The computer simultaneously displays the real-time video data and the real-time hand analysis data.

BRIEF DESCRIPTION OF THE DRAWINGS

In the Figures:

FIGS. 10a to 10d show jab and uppercut data in the form of graphs and corresponding punch depictions according to an exemplary embodiment;

DETAILED DESCRIPTION

Reference will now be made in detail to the preferred embodiments of the present invention, examples of which are illustrated in the accompanying drawings.

Figure 1:
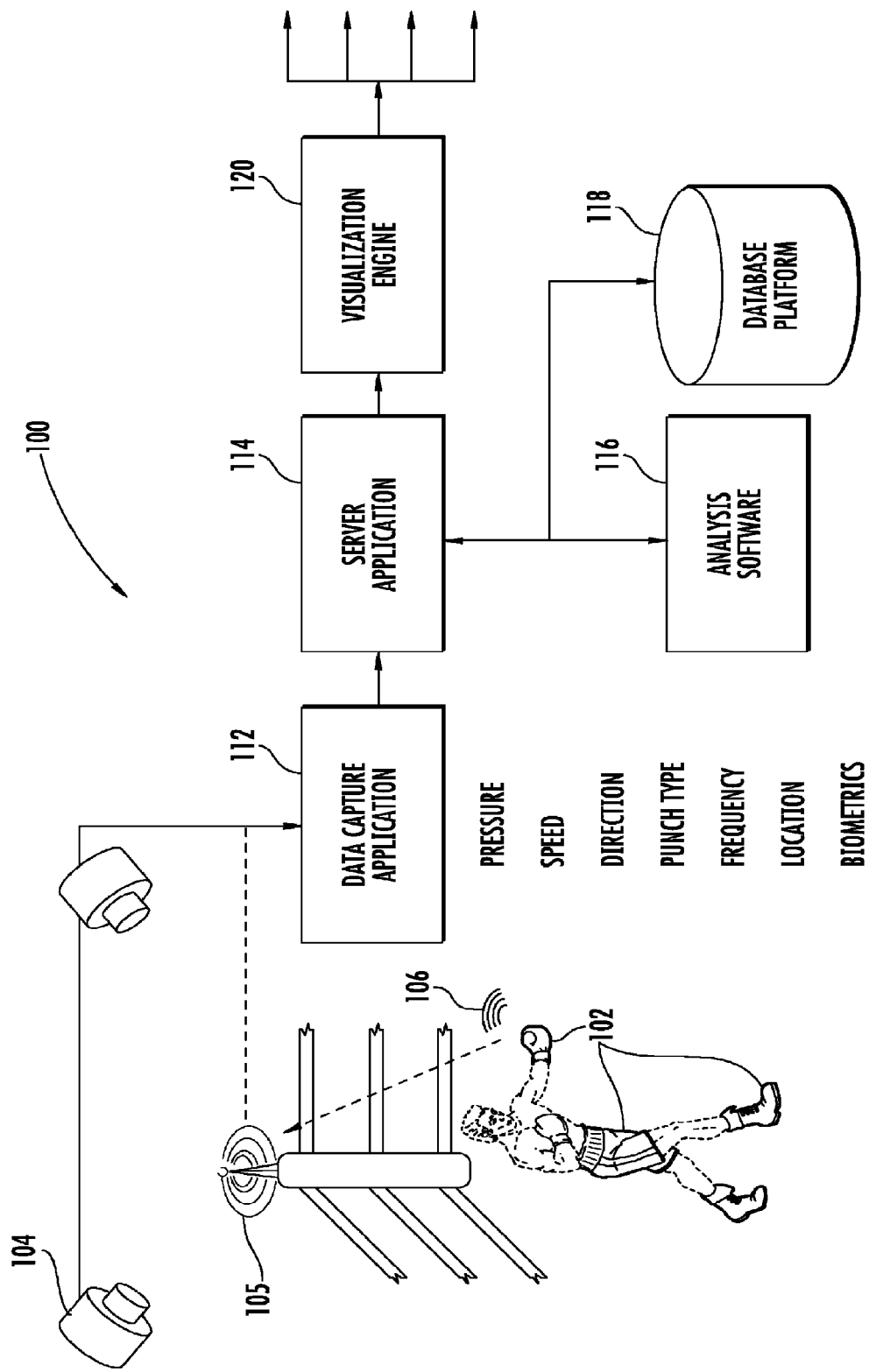
FIG. 1 shows an overall system design according to an exemplary embodiment.

FIG. 1 shows an exemplary system for capturing and analyzing activity-related data on an athlete 100. The exemplary system 100 can include, among other components, at least one sensor 102 or other data capture device 104, a signal strength monitor 105, and a transmitter 106 connected to the sensor 102 or data capture device 104. The sensor 102 can be positioned within equipment on the athlete to collect data regarding acceleration, force, orientation, or impact and transmit this data through the transmitter 106 to a data capture application 112 on a computer with a receiver (not shown). For example, in boxing, sensor data can be collected and analyzed for determining the speed and vector of a punch. The signal strength monitor 105 can judge the distance of the transmitter 106 or other radio device from the monitor using the strength of the signal. Data from multiple signal strength monitors 105 can be used to calculate the location of an athlete, or even parts of the athlete. The sensor 102 and/or data capture device 104, such as a camera, can provide activity-related data that is transmitted from the athlete's equipment to the computer, where it can be stored in a database and analyzed.

The computer connected to the sensor 102, data capture device 104, signal strength monitor 105, and/or transmitter 106 can execute a data capture application 112, a server application 114, analysis software 116, a database platform 118, and a visualization engine 120. The data capture application 112 receives input data from data capture devices 104 and sensors 102 and stores them in a memory, such as RAM, a hard drive, a database, or flash memory. A server application 114 has access to the data stored by the data capture application 112 and coordinates the data with analysis software 116, the database platform 118, and the visualization engine 120. The analysis software 116 compares the received data with historical data in the database. The analysis software then sends the results of its analysis to the server application 114. The server application 114 sends the analysis results to a visualization engine 120 that displays the results. Each application can be on a single computer or on separate computers connected through a network or the internet.

Figure 2:
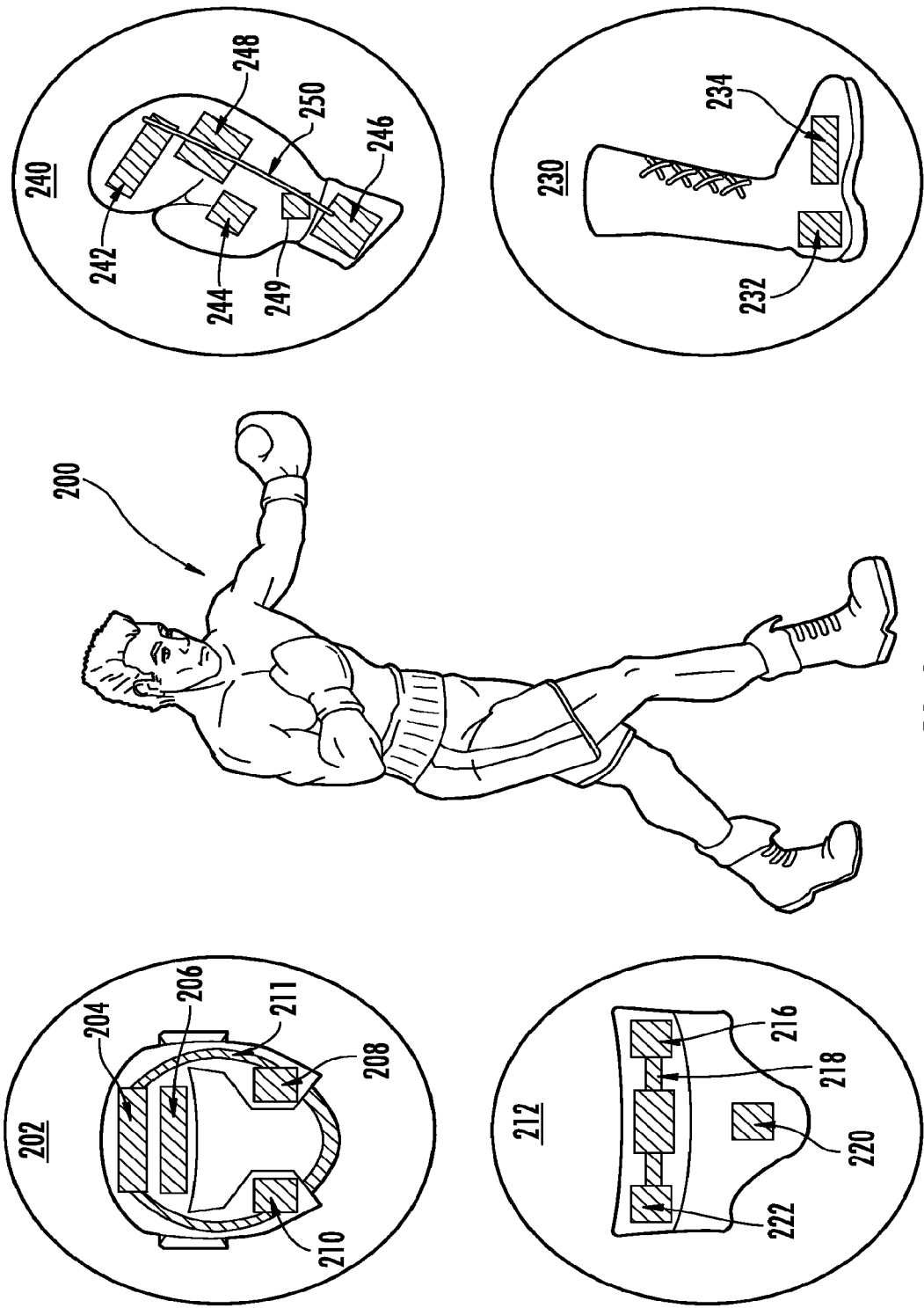
FIG. 2 shows various available data sensors and locations on a boxer's body according to an exemplary embodiment.

FIG. 2 illustrates various sensors and data capture devices that can be positioned within the equipment and clothing of an athlete 200. In one embodiment, an athlete can wear headgear 202 having a biometric sensor 204, a motion capture surface 206, and a force sensor 208. The biometric sensor 204, such as a temperature sensor, can be positioned between the headgear pads and the forehead of the athlete, monitoring the temperature of the athlete during an event. The motion capture surface 206 can be a surface coated with retro-reflective material to reflect light at a camera. A camera can be fitted with a filter so that only infrared light is sampled. Since the retroreflective material is more reflective than the rest of the materials used, the camera can effectively ignore the background. The force sensor 208 can also be positioned near the forehead on the headgear 202 to sense when and how forceful contact is made with the headgear 202. The headgear 202 can also have a microprocessor and wireless transmitter board 210 to transmit the data captured by the sensors on the headgear 202 to a computer running a data capture application. The sensors 204, 208 can be connected to the microprocessor through a wired transmitter 211. The microprocessor is on the same printed circuit board as the wireless transmitter, which can transmit collected data to a computer.

The athlete 200 can wear a waist guard 212 having a force sensor 214, a biometric sensor 216, a motion capture surface 220, a microprocessor and wireless transmitter board 222, and a wired transmitter 218 connecting the sensors 214, 216 to microprocessor. The sensors 214, 216 and motion capture surface 220 on the waist guard 212 can be used similarly to the sensors 204, 208 and motion capture surface 206 on the headgear 202.

The athlete 200 can wear a glove 240 that has a motion capture surface 244, a force sensor 242, an accelerometer 248, a gyroscope 249, and a microprocessor and wireless transmitter board 246. The motion capture surface 244 and force sensor 242 can be used similarly to the sensors on the headgear 202 and waist guard 212. The accelerometer 248 can be used to sense motions of the glove 240 during an event. A three-axis accelerometer can collect data on the motions of the glove 240 in a three dimensional space. A gyroscope 249 can be used to collect data on the orientation of the glove 240, allowing for the calculation of the rotation of the wrist and glove 240. This data can be used in motion analysis of the glove 240, for example, the type of punch thrown by a boxer. The sensors 242, 248, 249 can be connected to a microprocessor and wireless transmitter board 246 to transmit the data from the glove 240 to a computer.

The athlete 200 can also wear footwear 230 having a motion capture surface 232 and a sensor, microprocessor, and wireless transmitter board 234. The motion capture surface 232 can be implemented like the headgear 202 and waist guard 212. The sensors on the footwear 230 can include accelerometers to measure the motion of the athlete 200. The data collected by the sensors can be transmitted to a computer and analyzed as discussed in the glove 240 embodiment.

The sensors and data capture devices depicted on any one article of the athlete's clothing can be similarly used on other articles of clothing. For example, an accelerometer can be positioned within headgear 202 to capture data about the athlete 200. The sensors can also be positioned in different places within the gear or clothing. Further, the sensors can be placed on the same printed circuit board as the processor and transmitter or the transmitter can be separate from the processor.

Figure 3:
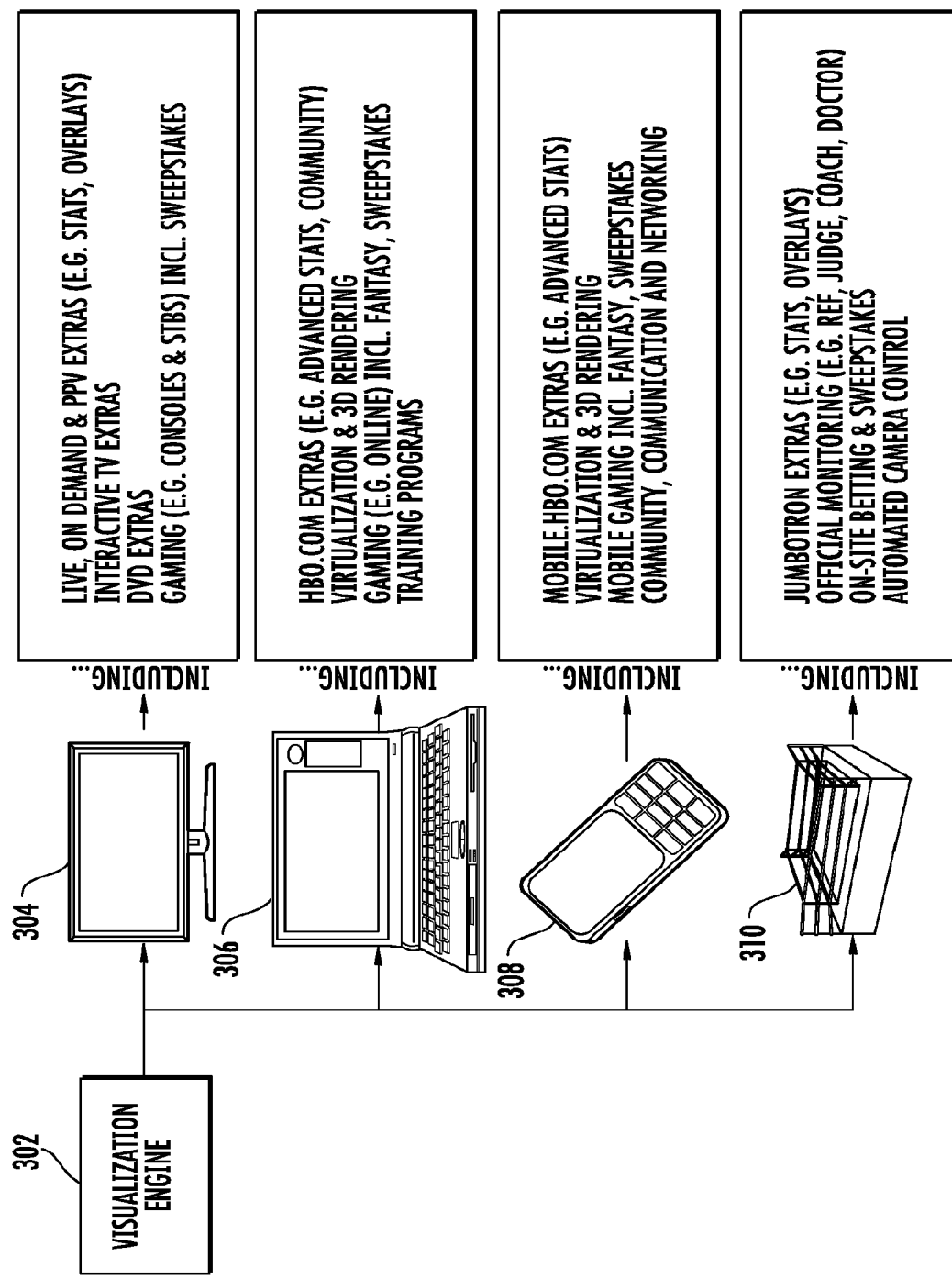
FIG. 3 shows various available end uses according to an exemplary embodiment.

FIG. 3 shows various aspects that can be implemented by the system in FIG. 1. A visualization engine 302 can process information including enhanced statistics, interactive visualizations, real-time information for officials and advanced athletic training programs. The visualization engine 302 can interact with a television 304 to display live, on demand, pay per view, DVD, Blu-Ray, Interactive television, and gaming extras. Extras include enhanced statistics, interactive visualizations, and real-time information. The television display can interact live with the content of the visualization engine by sending signals to and from a cable box. The television display can interact with a visual storage medium such as a DVD or Blu-Ray Disc by embedding information about the athletic activity in the DVD or Blu-Ray Disc. The visualization engine 302 can interact with computers 306 for computer extras, virtualization and 3D rendering, gaming, and training programs. The visualization engine 302 can also interact with mobile devices 308 such as cell phones and smart phones to display mobile extras, virtualization and 3D rendering, mobile gaming, and create a mobile community with communication and networking.

The exemplary system 100 can also provide support for live events 310. Similar to televisions, statistics and overlays can be displayed on a large scale display such as a Jumbotron screen at live events. The system can analyze data to detail how tired an athlete is by trending and/or tracking the speed and force of the athlete's motions. The system 100 can also interact with and display information for officials such as referees, judges, coaches, trainers, and doctors to monitor athletes at an event. Also, the system 100 can be used to display extras on monitors for on-site gambling and sweepstakes. The system 100 can also be used at a live event 310 for automated camera control.

Figure 4:
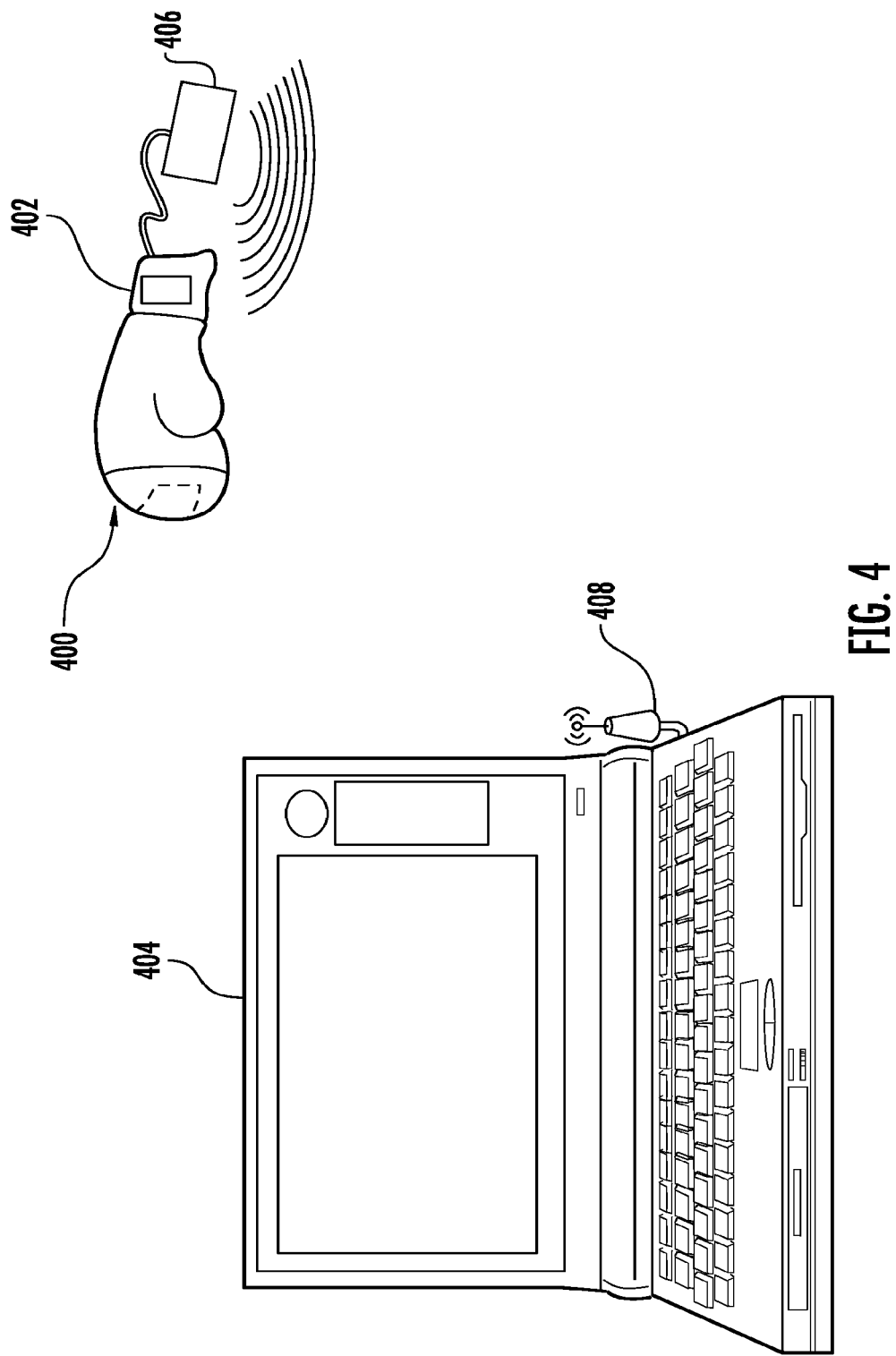
FIG. 4 shows a system for transmitting data from an item of athletic equipment to a computer according to an exemplary embodiment.

In one exemplary embodiment, sensors and other data capture devices can be placed on a boxer. FIG. 4 illustrates how data can be transmitted from a piece of equipment on the boxer's hand or wrist, such as a boxing glove 400 or a cuff 402 to a computer 404. The cuff 402 can be wrapped around the boxer's wrist and positioned over or under a cuff of the boxing glove 400. The boxing glove 400 has the advantage of being capable of having more sensors, such as contact sensors, than the cuff 402. The cuff 402 has the advantage of being used with multiple boxing gloves. A sensor and wireless radio board 406 can be a printed circuit board that can transmit the data captured from the sensors to a receiving board 408 connected to the computer 404. The receiving board 408 can be a radio for receiving information from the sensor and wireless radio board 406 or can have additional functionality, such as data processing. The sensors are not required to be positioned on the same board as the wireless radio, but can be positioned on the same board to save space and weight.

Figure 5:
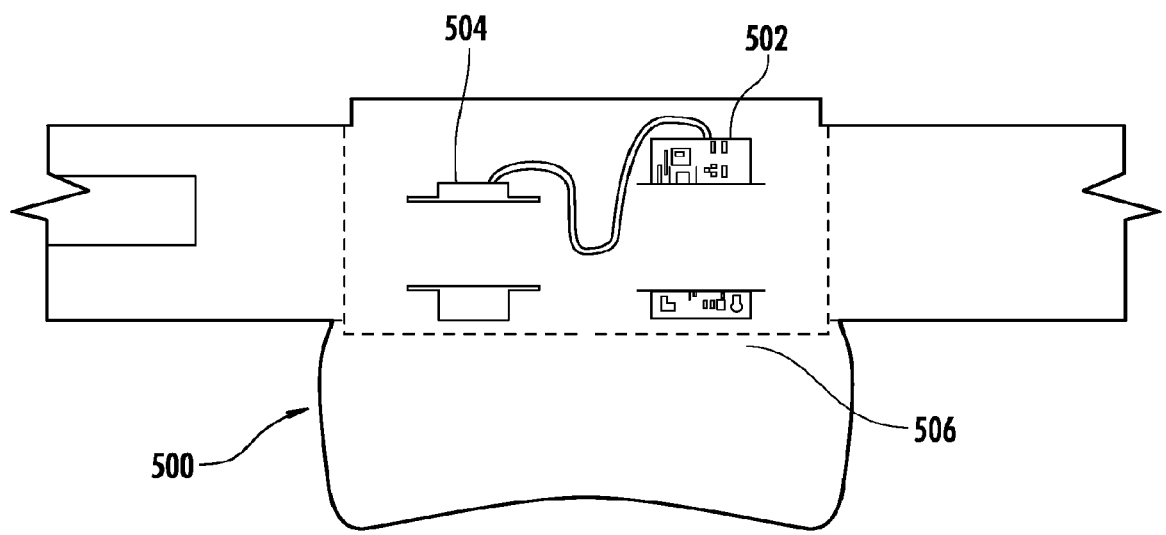
FIG. 5 shows a boxing glove cuff adapted to hold sensors according to an exemplary embodiment.

As shown in FIG. 5, a cuff 500 can have a wireless sensor board 502 connected to a battery 504 positioned within the cuff 500. The cuff 500 can be constructed of foam material to protect the wireless sensor board 502 and battery 504. Additional foam 506 can be folded over to create a cuff pouch that the wireless sensor board 502 and battery 504 can easily slip in and out of. The mobility of the wireless sensor board 502 and battery 504 helps with troubleshooting in the field because one board or battery can be replaced by another. Due to the miniature size of the wireless sensor board 502 and battery 504, a boxer can comfortably wear the cuff 500. The wireless sensor board 502 and battery 504 are also light for the convenience of the boxer.

Figure 6:
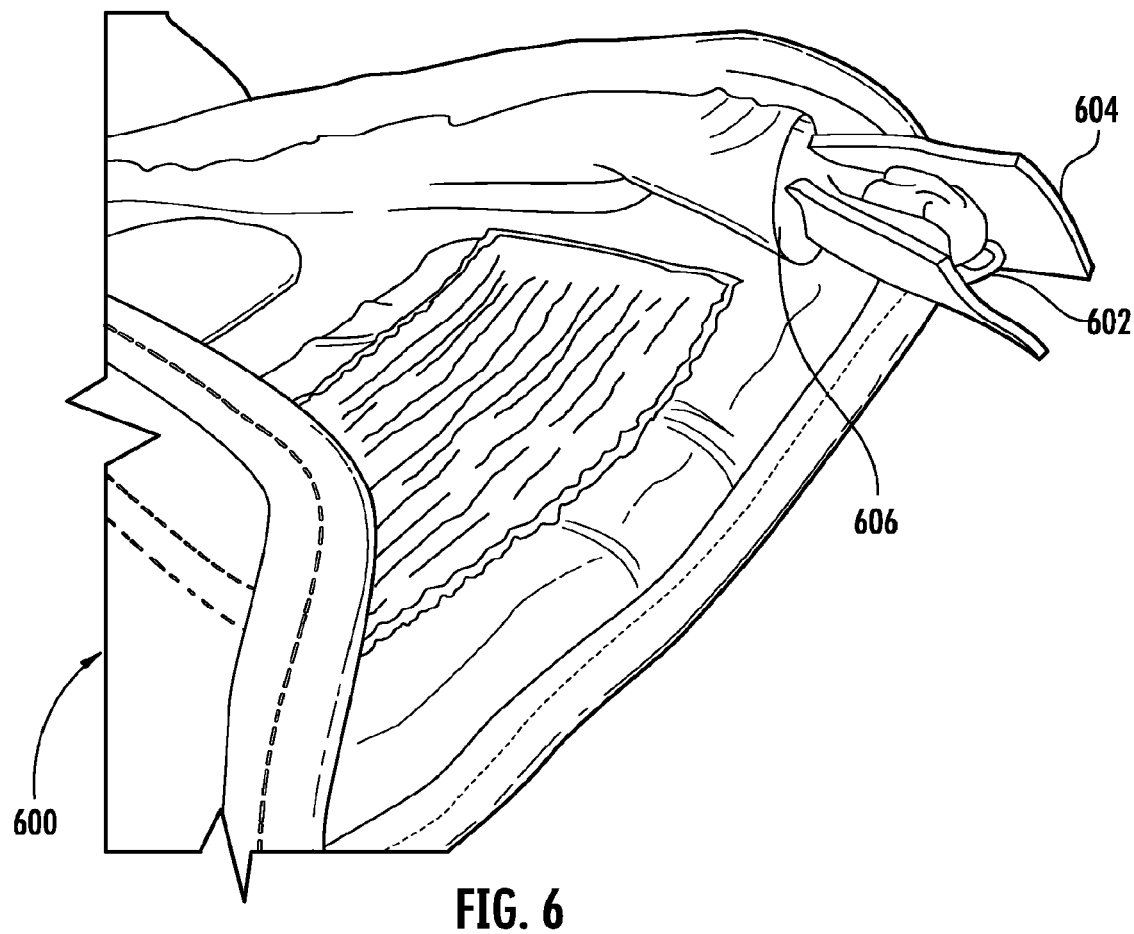
FIG. 6 shows a boxing glove adapted to hold sensors according to an exemplary embodiment.

In another embodiment, a battery and wireless sensor board 602 can be placed in a boxing glove 600, as shown in FIG. 6. A foam layer 604 around the wireless sensor board 602 can protect the board. With this protection, the wireless sensor board 602 can be slipped into a pocket 606 in the glove 600. The wireless sensor board 602 is positioned on the on the forearm side of the boxing glove 600 so the board does not absorb a direct hit to the outside of the boxing glove 600. The mobility of the wireless sensor board can allow for quick troubleshooting and replacement. The wireless sensor board 602 can also have inputs for sensors positioned within the glove 600. The glove 600 can have internal sensors connected through a conductive ribbon or wire to the pocket 606. As in the cuff 500 embodiment, the wireless sensor board 602 does not have to be a single unit.

Figure 7A:
FIGS. 7a to 7e show various perspective views of a soft switch assembly according to an exemplary embodiment.
Figure 7B:
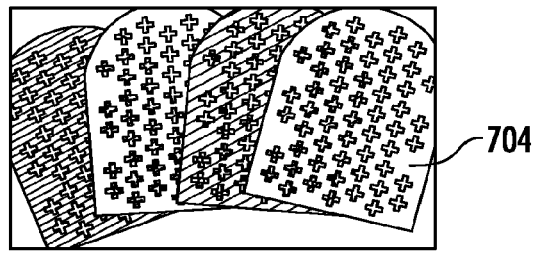
Figure 7C:
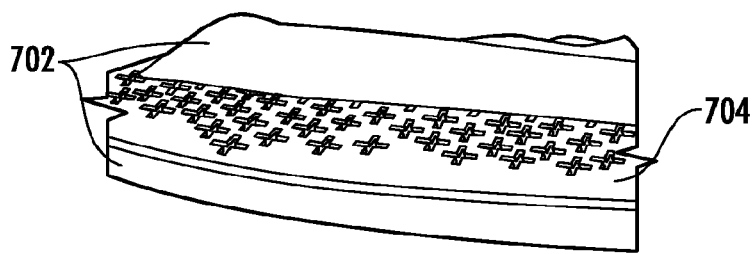
Figure 7D:
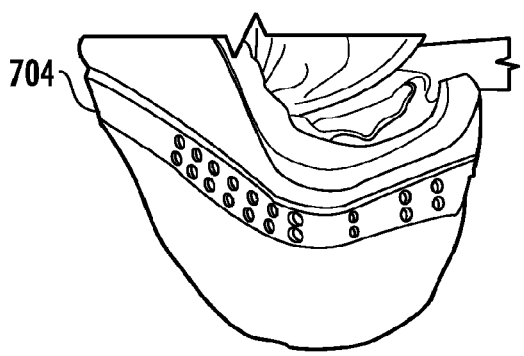
Figure 7E:
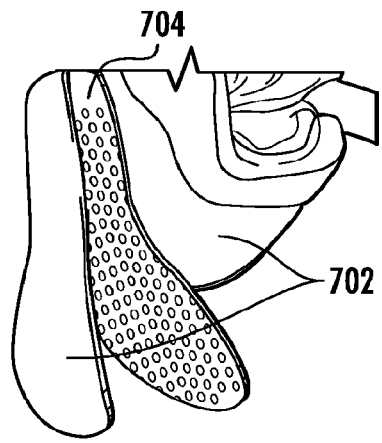
Figure 8:
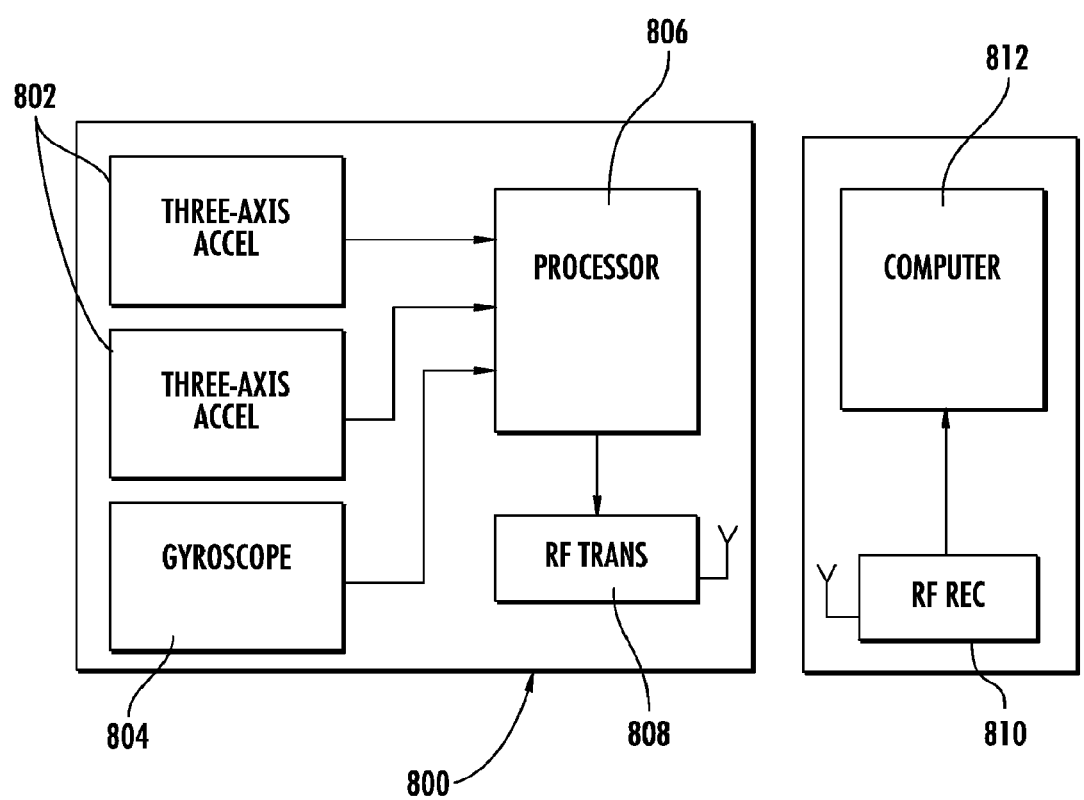
FIG. 8 shows a system for collecting data from sensors according to an exemplary embodiment.

In yet another embodiment, as shown in FIGS. 7a to 7e, a soft switch can be positioned within a boxing glove to indicate when an impact on the boxing glove has occurred. A soft switch can be constructed out of two layers of conductive fabric 702 separated by a non-conductive mesh 704 sewn into the punching face of the glove. FIGS. 7a and 7b show a plurality of non-conductive meshes with varying densities. A charge is applied to the conductive fabric 702. When non-compressed, the mesh fabric 704 separates the two conductive fabrics so no current can flow between the two conductive layers. Current can only flow when the glove strikes a target with enough force to temporarily press the two pieces of conductive fabric 702 together through the holes in the mesh. When the face of the glove is compressed by the contact, the two conductive panels 702 touch through the mesh 704, closing the switch and indicating an impact. A plurality soft switches can be used to determine what face of a glove made impact. Further, switches with different mesh density can be used to approximate force. By placing multiple soft-switches with varying mesh sensitivities in a glove, force can be coarsely approximated. A different amount of force would be required to compress soft-switches with different density meshes. The switch can be attached to a conductive ribbon that leads to the pocket 606 in the glove 600. The conductive ribbon can be attached to the wireless sensor board 602 allowing for synchronization and transmission of the sensor data.

A property of any switch is bounce, which is multiple contacts of the switch in the space of a few milliseconds. Bounce leads to a false reading of the switch, as it may indicate multiple closures when only one effective closure occurred. A bounce can be corrected by circuitry using a capacitor and a resistor or by software to compensate for the bounce. According to known methods, the switch data can be processed to account for the bounce once transmitted from the wireless sensor board 602 to a computer, which could save battery life.

Various sensors can be placed on the wireless sensor board 800 to capture data of a boxer's punch, including accelerometers 802 and gyroscopes 804. Accelerometers 802 can be positioned on the sensor board 800 to provide data on the acceleration of boxer's punch. Accelerometers 802 on the board 800 can have multiple axes. Three-axis accelerometers are available or can be built by using multiple single-axis or dual-axis accelerometers having the axes arranged orthogonal to each other together, thereby creating at least X, Y, and Z axes. Acceleration data can be measured on each of the axes and the data on the axes can be correlated to show movement of the wireless sensor board 800 in three dimensions.

Many currently available accelerometers have low range, high resolution capabilities or high range, low resolution capabilities. Accelerometers calculate acceleration, a common unit to measure acceleration is the acceleration due to gravity, g. 1 g=9.8 m/s$^2$. A low range accelerometer may have the range of about 0 g to 6 g. This range would be insufficient to monitor the acceleration of a punch because the punch of a boxer can be in excess of about 100 g. Multiple accelerometers with varying ranges and resolutions can be used to collect more complete data on a boxer. For example, a low-range accelerometer with the range of about −3 g to +3 g can be used in conjunction with medium-range accelerometer with a range of about −18 g to +18 g, and a high-range accelerometer with a range of about −100 g to 100 g. The lower range accelerometers can generate more precise data during the initial acceleration and deceleration phases while the high-range accelerometer can be used to calculate maximum acceleration.

Figure 9:
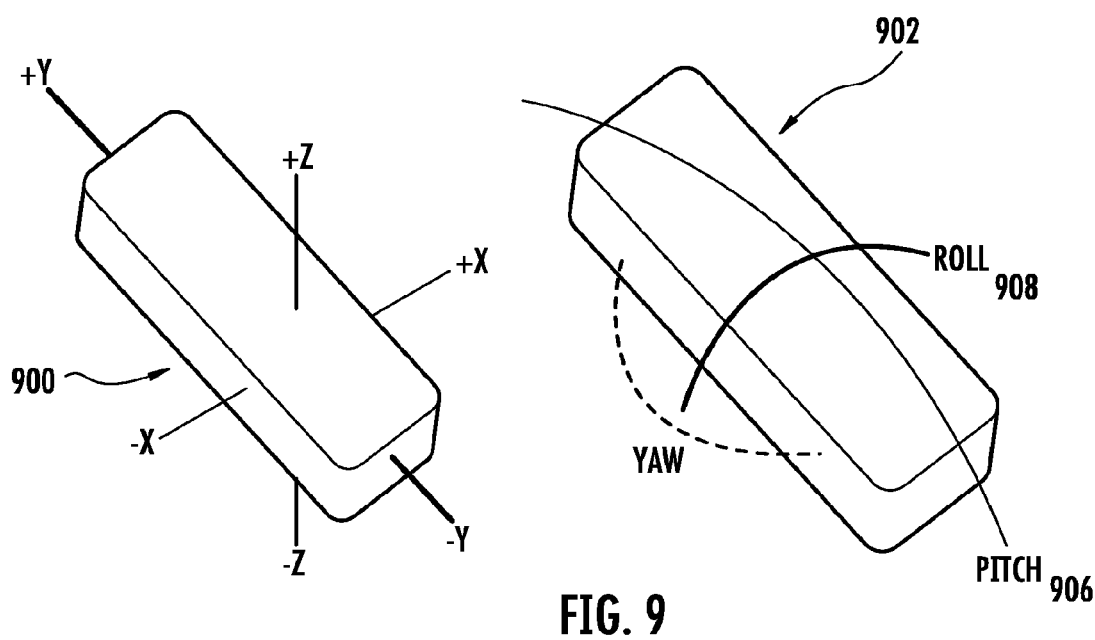
FIG. 9 shows an accelerometer according to an exemplary embodiment.

FIG. 9 shows how a 3-axis accelerometer 900 can be used to calculate orientation. The sensors generate data that about the instantaneous acceleration rates on all three axes. Correlation of this data on a sensor 902 yields tilt values in the form of pitch 906 and roll 908 by using earth's gravity as a reference point. Pitch 906 can be found by calculating the angular difference between the z-axis location and the force of gravity by correlating the force of gravity on the y-axis. Roll 908 can be found by calculating the angular difference between the z-axis location and the force of gravity by correlating the force of gravity on the x-axis.

A gyroscope 904 can also be placed on the sensor board to provide data on the angular motion of a first as it moves through space. A gyroscope measures angular acceleration. A gyroscope can measure the orientation of an object independent of its acceleration. Yaw, pitch, and roll can all be determined by a gyroscope, a gyrometer, or an angular motion sensor. A gyroscope can sense angular rate change, for example at −500 degrees to +500 degrees each second. A multiple-axis gyroscope can be used to get complete angular motion data in a three dimensional space. Examples of a gyroscope are the InvenSense IDG-300 and IDG-600. One axis can be used to sense yaw, a second axis for pitch, and a third axis for roll.

The sensors can be either digital or analog. If the sensors are analog, an analog to digital converter may be necessary to convert the data into a digital signal to be used by a processor 906. Many micro-controllers available today contain built-in analog to digital converters. The processor 906 can then format the data so it is suitable for transmission. The processor can store the data in its own memory or external memory until transmitted.

Data can be collected at one frequency and stored in the memory of the processor 906. Then, the processor 906 can transmit the data through a Radio Frequency (RF) Transmitter 908 to an RF Receiver 910 connected to a computer 912. The computer 912 can store the information in various ways, such as a database table. The computer 912 can analyze the data or send the data to another computer to analyze the data. Multiple transmitters used at the same time can be on different frequencies to minimize radio interference and possible data loss. Various transmitters and receivers can be used, including, but not limited to, Bluetooth, 802.11g, 802.11n, and other radios.

The collection of data by the processor 906 can be synchronized so that the data collected can be processed together. One way of synchronizing is by using a single clock signal for all sensor readings. Analysis software can then analyze the data in real time, with each data point on each sensor corresponding in time with the other sensors. Synchronization can also occur by timestamping the data to a common clock, thereby allowing for some of the data to be sensed at different frequencies. The timestamps also allow for synchronization by the analysis software of multiple sensor boards. This can be accomplished because the analysis software will have the data of the clock frequencies and time stamps of each of the boards. These boards can be synchronized prior to use so the analysis software can analyze data on multiple sensor boards at the same time.

In one embodiment, a thrown punch is detected and identified as a punch event within a stream of continuous data. A thresholding scheme combines the acceleration along all three axes to detect and identify the punch. When a value exceeds a preset threshold limit, the system can register a punch and begin analyzing the continuous data to determine the type, motion, and other statistical data of a punch. Complete analysis of a punch can take into account data that occurs before the threshold limit is passed.

The raw data collected by the accelerometers and gyroscopes can be used to calculate instantaneous measurements. Such measurements include the speed of each punch, the force of each punch, the duration of each punch, the distance covered by each punch, and other movements of the first during a punch.

The speed and velocity of a punch can be determined by integrating the acceleration from a starting point using accelerometer data: $v(t)=\int a(t)+v1$. Because the acceleration data is in digital format when a computer processes it, discrete mathematics and a summation can be used for the calculation. The computer processing the data can accommodate for gravity by calculating the direction of gravity in relation to the axes of the accelerometers when the sensors sense approximately only the force of gravity (9.8 m/s$^2$). The processing computer can calculate the direction of the force of gravity during motions thereafter by correlating accelerometer and gyroscope data.

The distance covered by each punch can be determined over the time of the punch: $d(t)=\int v(t)$. Acceleration starting at a fixed point can be integrated to calculate speed at a given time. The speed can be integrated to calculate distance.

Sensor data can be analyzed to determine the force of a punch. Force is equal to the product of mass times acceleration, or $F=ma$. Mass is how much matter is present in an object, while acceleration is the change in velocity over time. The force of a punch can be determined using the deceleration of the first at the time of impact of the punch and the mass of a boxer's arm. The mass of a boxer's arm can be approximated by calibration. A boxer equipped with a sensor glove can punch a force sensor, like a force sensing resistor. The force sensor determines the force of a punch. The accelerometer determines the acceleration of the punch. Using those two data points, we can determine the approximate mass of the boxer's arm for that particular type of punch. The approximate mass of the boxer's arm for a particular type of punch can be used as a constant to approximate the force of a boxer's punch. The approximate mass of a boxer's arm can be profiled so that different types of punches by a particular boxer have different approximate masses. This is to account for how much of a boxer's body is used during a particular type of punch. Multiple profiling rules can be created for a boxer.

The duration of each punch can be found by using a clock to time a punch starting when acceleration starts and ending at hit, block, or miss. If a thresholding level is used as a cue that a punch has begun, analysis software can be used to determine when the punch actually started, not just when the threshold was met. A rule can be set so that a punch starts when a sharp acceleration begins. Deceleration data can be used to determine when the punch ended.

A sharp deceleration during a punch event can indicate a hit. For example, when an uppercut hits the abdomen of an opponent, the uppercut decelerates sharply due to the hit. A sharp deceleration is also seen when a jab hits the head of an opponent. In this case, though, the sharp deceleration is not the end of the movement, rather the sharp deceleration is part of the a complete follow through motion. Multiple rules can be set for when a punch event has ended and a hit is registered.

A block can be indicated by a lateral movement of the first during the course of a punch revealed by an acceleration to the side with a forward deceleration. Additional information can be taken from an opponent's gloves registering a blocking motion at the same time as the punch event. The data from both boxers can be correlated to show both a punch and block. A block motion by the defender can be recorded as a lateral motion of the glove, as well as an inward motion by the glove at the time of an impact. The motion can be indicated during the punch event by the offensive opponent. Multiple rules can be set for when a punch event has ended and a block is registered. Data from both boxers can be profiled and rules set up for both individuals, as well as general rules.

A missed punch can be indicated by a slow forward deceleration along with a completed punch movement. A completed punch movement can be set as a rule. Accelerometer data not indicating a hit or block deceleration during the course of a punch event can be considered a miss outcome. Multiple rules can be set for when a punch event has ended and a miss is registered. Different punch types can have different miss endpoints. Other end outcomes can also be registered, such as a deflection.

Lateral and other movements of the first during a punch can be identified through data on lateral acceleration. Lateral acceleration can be calculated by correlating accelerometer and gyroscope data. As a punch moves forward, lateral acceleration can be determined as being perpendicular with the forward acceleration and parallel to the ground. The acceleration in combination with orientation data can be used to determine lateral movements. Other movements can include guarding and blocking during the punch movement of the opponent.

Sensor data can be analyzed to determine the type of punch thrown. The type of punch can be determined by using gyroscopes, accelerometers, or both in combination. Vertical, outward, and forward acceleration as well as wrist movements can be determined by correlating gyroscope orientation data and accelerometer data. A computer can be programmed with a set of rules defining each type of punch. A punch can then be determined by comparing the live or recorded data with the set of rules. The rules can be in the form of pre-identified motions or outcomes.

FIG. 10a depicts a jab motion along an x-axis. The motion can also be detected in three dimensions, but is simplified in this example to two axes. A jab starts from a block position 1002a, then moves forward with a twisting of the wrist 1002b and ends with the palm faced down and the arm extended 1002c. Gyroscope data shows that a jab goes from a roughly vertical orientation 1002a while in guard position, moves straight out from the leading shoulder 1002b, and rotates approximately 90 degrees to finish with the palm facing downward 1002c at the end of the punch. Accelerometer data shows that a jab is a fast acceleration from the leading hand in a direction away from the boxer's body. The data can be used to create a rule for a complete jab motion and the rule can be stored in a database. Pre-identified motion patterns can also be used to create the rule. A separate jab rule can be created for a jab that hits. The rule can include a sharp deceleration of the punch followed by a follow through on the motion. Different rules can be set up for different stages of completion of the punch before deceleration. Multiple rules for jabs can be created, some specifically calibrated to an individual boxer.

FIG. 10b shows an uppercut motion occurring on a z-axis and an x-axis. The motion can also be detected in three dimensions, but is simplified in this example to two axes. An uppercut is a close proximity punch with vertical movement and a small forward motion. An uppercut can start from a guard position 1004a, then the accelerometer data would show a vertical acceleration with a small forward component. The motion can be viewed as parabolic, with the motion being completed 1004b as the boxing glove comes back towards the boxer. The boxer's wrist also twists so that the inside of the first comes towards the boxer. A gyroscope will indicate the twisting of the wrist at roughly 45-90 degrees from the beginning of the punch to the end. The data can be used to create a rule for a complete uppercut motion and the rule can be stored in a database. Pre-identified motion patterns can also be used to create the rule. Separate rules can be created for when an uppercut that hits an opponent. Accelerometer data can indicate a hit by having a sharp deceleration in the forward and vertical movement. Different rules can be set up for different stages of completion of the punch before deceleration. Multiple rules for uppercuts can be created, some specifically calibrated to an individual boxer.

FIG. 10c depicts a right hook on an x-axis and y-axis. The motion can also be detected in three dimensions, but is simplified in this example to two axes. A left or right hook is a punch with little vertical movement with a component of outward, forward, and inward motion. From a guard position, the punch can be seen as moving outward 1006a. The punch moves forward and outward 1006b, then begins to turn inward 1006c. The hook is completed with the first moving inward 1006d towards an opponent. The accelerometers will show the movement as forward and outward, and then forward and inward. The gyroscope will show the twisting of the wrist with the palm facing downward at the end of the punch. Data can be used to create a rule for a complete hook motion and the rule can be stored in a database. Pre-identified motion patterns can also be used to create the rule. Separate rules can be created for when a hook hits an opponent. Accelerometer data can indicate a hit by having a sharp deceleration in the forward and inward movement. Different rules can be set up for different stages of completion of the punch before deceleration. Separate rules can be created for hooks, some specifically calibrated to an individual boxer.

A soft switch, described above, can be coupled to the accelerometers and gyroscopes to add an additional data point to complement acceleration data. The soft switch can help analyze the data by giving a time of impact. Impact can be used as a point for when a hit occurs, when a block might occur, and when a miss occurs. A hit or blocked punch can register data indicating the time of impact. With the time of impact as a reference, the follow through of a punch can be analyzed. A miss can occur when a punch is completed without any impact.

Motion and punch data can be profiled and stored in a database. A particular boxer's punches and motions can also be profiled to create a boxer specific motion profile. The profiles can go into even more detail and track changes in motions between different rounds of a boxing match. Profiles can include data and rules about pre-identified motions or outcomes. For example, one outcome can be a jab. As discussed, the timing, acceleration, and angular rate change data for this type of motion and outcome is different than that of an uppercut. FIG. 10d graphically illustrates how sensors could read different data for the motion of a jab and the motion of an uppercut. The graphs show the X, Y, and Z axes of an accelerometer as well as the X and Y orientation of a gyroscope during the course of a jab and a subsequent uppercut. The accelerometer and/or gyroscope data can be used to identify a jab or uppercut. Similar analysis can be used to detect the outcome of a punch, whether a punch landed, missed, or was blocked. The orientation of the gloves and little acceleration of the fists can represent a profile for the automatic detection of a boxer's stance.

Figure 11:
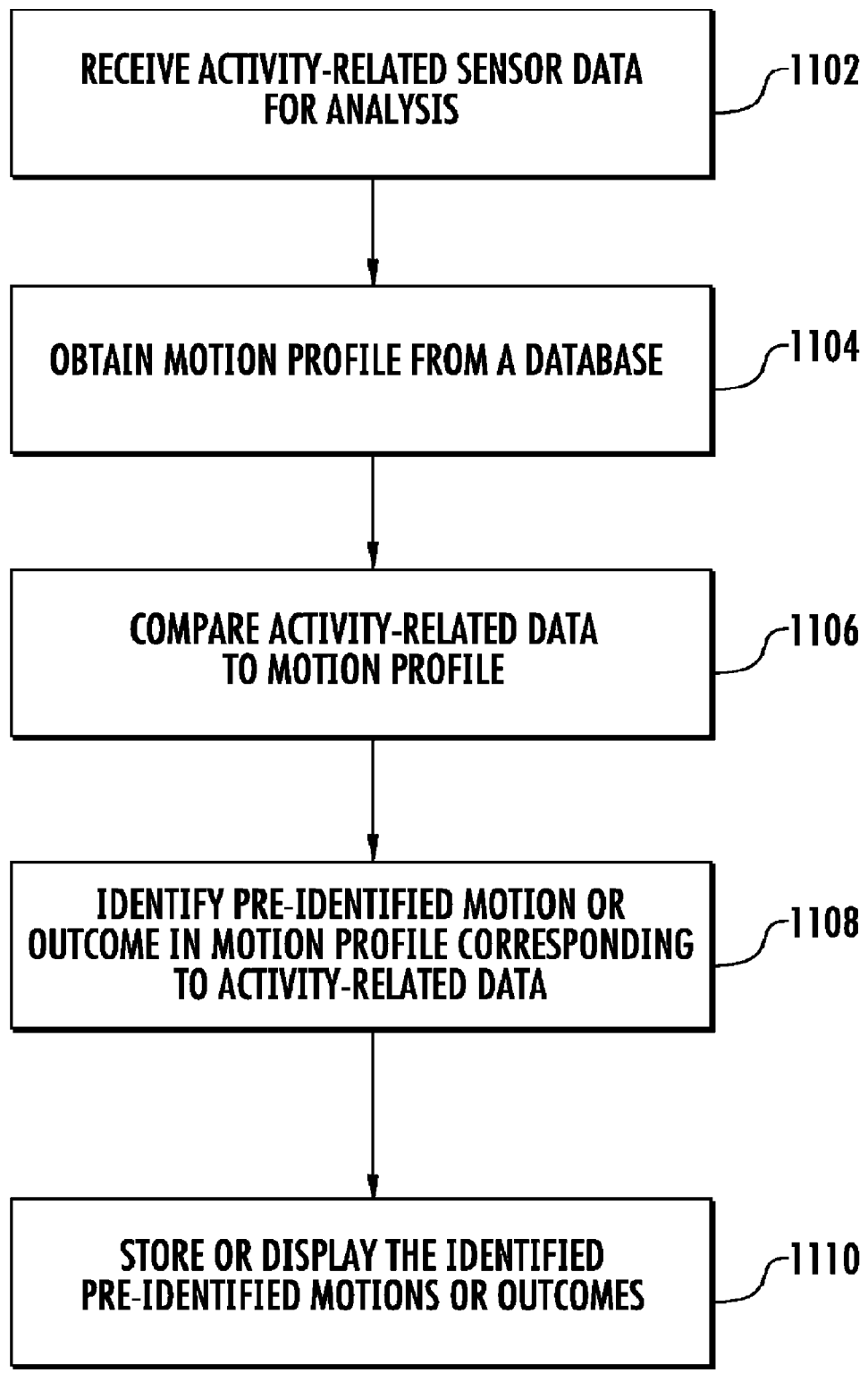
FIG. 11 shows a flow diagram of a method to analyze and display data according to an exemplary embodiment.

Analysis software can be used dynamically on the data collected by the sensors to qualitatively determine whether a punch has been thrown, and if so, what kind of punch was thrown. The software can be implemented on known devices such as a personal computer, laptop, a special purpose computer, a server, and various other devices with processors. This software can be stored on a computer readable medium and can execute programmable code on a general purpose computer. FIG. 11 illustrates an exemplary method to analyze the data dynamically.

A computer running analysis software 1102 receives activity-related sensor data. A transmitter can send data wirelessly from the sensors to a radio connected to the computer. The computer can process raw data into more usable data structures, such as a punch event. The computer can recognize a punch event as a data on an accelerometer accelerating past a threshold value.

Once a punch event has been detected, the punch can be analyzed. The computer obtains a motion profile from a profile database 1104. The database can contain rules for different punch types and punch outcomes. The database can be on a different computer, accessed through a network, or be pre-loaded onto the computer running the analysis software.

In stage 1106, the computer compares the activity-related data to the motion profile rules. Punch event data can be compared to general punch rules to narrow the type of punch into categories, such as a possible uppercut, hook, or jab. The categories are rules with broad punch data event possibilities. The rules can be construed at as a container for types of punches. The broader the rule, the more punch data that can fit within the container or category. The punch event data can then be compared to more specific rules within the general category.

In stage 1108, the analysis software can identify a pre-identified motion or outcome in the motion profile corresponding to the activity-related data. The motion rules can be compared to the punch event data to determine what type of punch occurred. Analysis can be used to determine the broad category of the punch event as well as more descriptive categories. A more descriptive categories can include a jab with a follow through, an uppercut with no follow through, a missed jab, and a blocked right hook. If an unknown motion is discovered, the motion will be added to the database and a description for the motion can later be filed. Outcomes can be the motions described above or in the form of conclusions, such as a hit, block, or miss. Outcomes can be determined by comparing outcome profile rules to the punch event data. Punch event data can be in the form of a raw data stream or data patterns.

Stage 1110 shows the computer storing or displaying the identified pre-identified motions or outcomes. An example of displaying the identified pre-identified motions or outcomes is by overlaying the analysis on a live boxing screen, such as a Jumbotron screen at an event, a television, or a website. Information that a certain type of punch was registered can also be stored in a database for later statistical analysis. The information can also be used to update boxer-specific motion profiles, both generally and round-by-round.

Another feature is software to generate statistics and score a boxing match or sporting event. In boxing, the system can count the number and types of punches thrown, landed, and blocked as identified by the analysis software. The computer can act as an unbiased and impartial referee. The scoring can be overlaid on a large-scale display at a live event, a television, or via a website, or stored in a database for future use.

Along with scoring and statistics, another aspect is software to determine trending during the course of an event. Trending includes the number of punches during an event, decrease in punch speed over the course of an event, the current most powerful or fastest punch of the night, and the most powerful or fastest puncher. The number of punches for each athlete and each hand can be counted throughout the night. Decrease or increase in punch speed throughout the course of an event can be determined by tracking the calculated speed of each punch thrown during the night by an athlete. All of this information can be shown on an overlay during the course of a live event.

Figure 12:
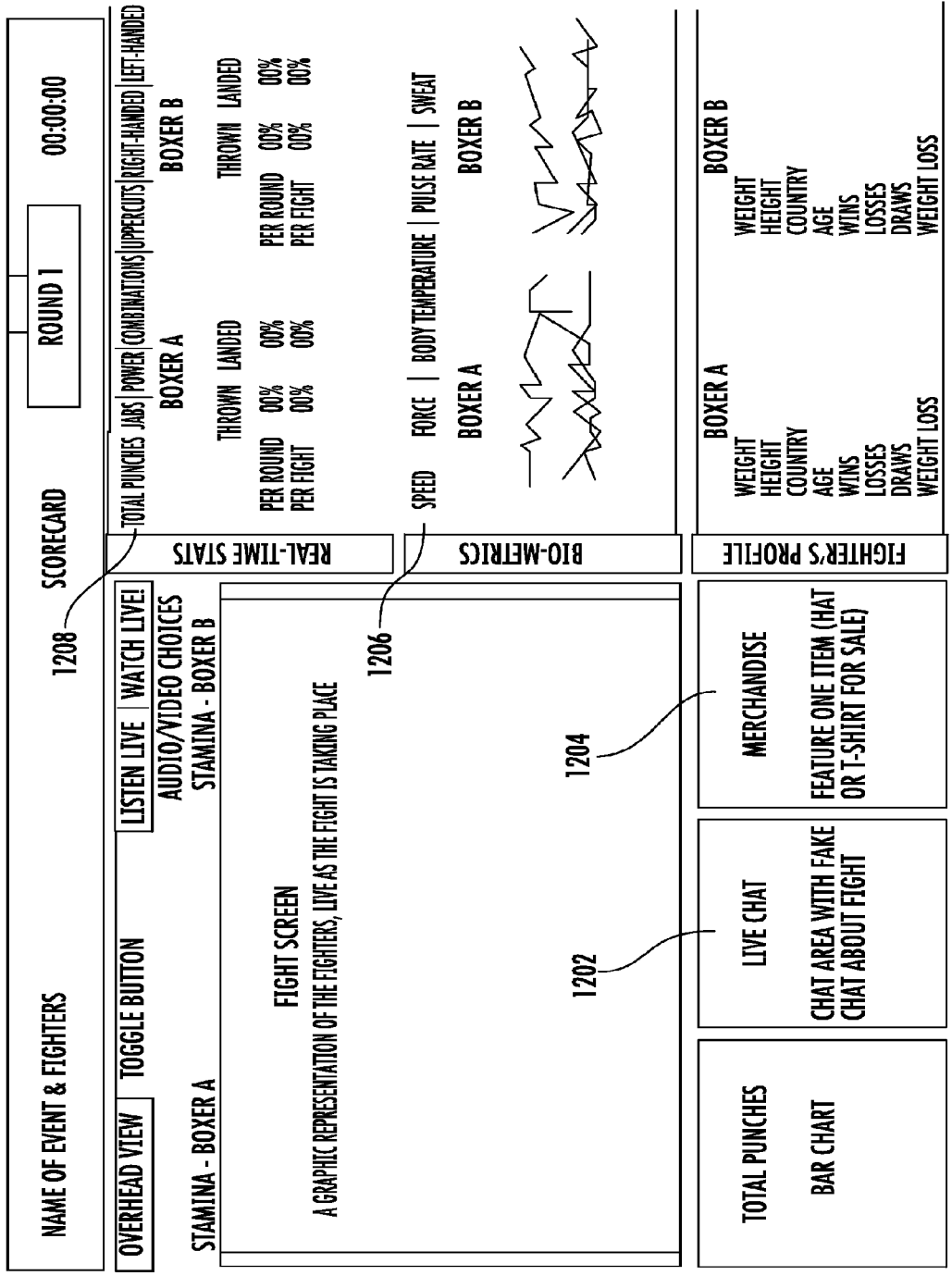
FIG. 12 shows a screen shot of boxing display data and analysis according to an exemplary embodiment.

FIG. 12 exemplifies an embodiment where data gathered and statistics can be overlaid on a screen. The screen can be either interactive or non-interactive. In an interactive screen, there can be options to chat 1202 or buy merchandise 1204. An interactive user can choose the overlaid information boxes 1206, 1208 to view information about an event and the athletes. A non-interactive user can see rotating information boxes.

Figure 13:
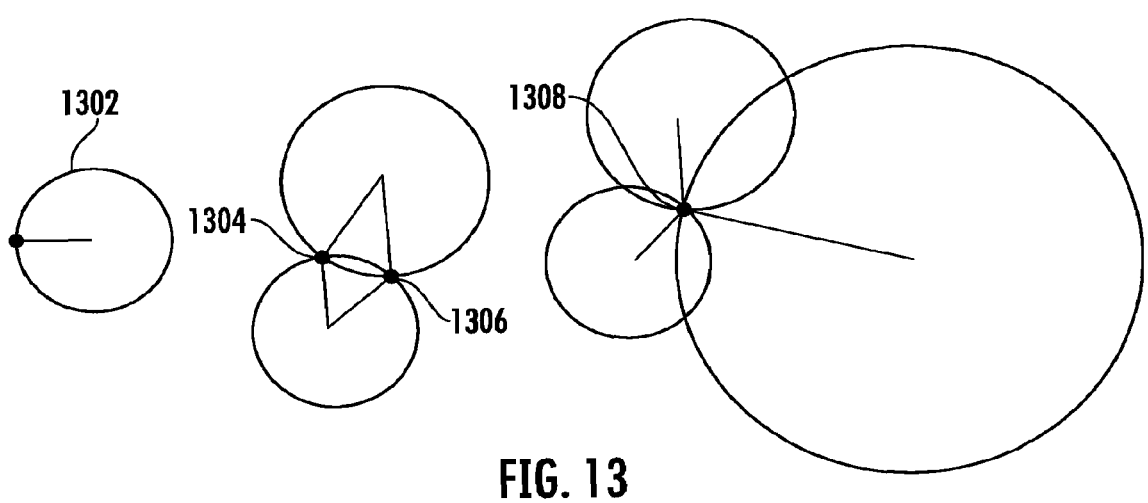
FIG. 13 shows a 2-dimensional representation of location triangulation according to an exemplary embodiment.

An exemplary system can also use the wireless radios on articles of clothing or equipment to triangulate the position of an athletes during an event. The signal strength of a radio on the athlete can be used to approximate the distance between a signal strength monitor and the radio. The signal strength monitor can also be a receiver. Distance from a signal strength monitor can be calculated using the inverse square law, signal strength=1/distance squared. The signal strength monitor can also be calibrated to ensure proper functionality. Calculating distance from a radio signal can be accomplished using existing technology. FIG. 13 shows a two-dimensional example of location tracking through triangulation. Using the distance as a radius, the location of the signal is narrowed to be on the perimeter 1302 of a circle. Location can be triangulated using multiple signal strength monitors. Adding a second fixed point of reference narrows the position of the radio signal to two points, 1304 and 1306. Adding a third fixed point of reference leaves one location point 1308 in two dimensions. Adding a fourth fixed point of reference allows for three dimensional tracking of the signals, using the surface of a sphere instead of a circle for tracking. More than four signal strength monitors can be used. The signal strength monitors can be placed in the corners of a boxing ring. Four monitors with known heights and locations can be used to create a three-dimensional virtual boxing ring to track the motion of the boxers. In an alternative embodiment, eight signal strength monitors fixed around a boxing ring can be used to track the motion of a boxer or the locations of radios on the boxer. For example, four signal strength monitors can be fixed at high locations and four can be fixed at lower locations, e.g., the base of the boxing ring.

In another embodiment, one or more cameras can be used to track the position of boxers during a boxing match. A single camera can be used to track athletes in two dimensions. A camera can be placed directly above the boxing ring. A high-resolution camera can distinguish the boxers as distinct from the floor of the ring. A computer can analyze the camera data frame by frame to track boxers. The data can be analyzed by a computer to show how a boxer is controlling the ring over the course of a round or fight, such as by counting the number of punches thrown, blocks used, position within the ring, or other collected data.

In another embodiment, multiple cameras can be used to capture the motions of the boxer's body. The motion capture can be accomplished using existing technology. Retro-reflective markers or motion capture surfaces can be placed on the body so the cameras can clearly distinguish between the body and the background. Placement of markers on the joints would allow for more detail, but markers on athletic clothing would interference less with a boxer. The images from the cameras can be used to create a virtual three-dimensional model or representation of the boxers in a space.

Retro-reflective markers may interfere with normal television camera operation. Therefore, an alternative to track the body instead of relying on retro-reflective markers is to use UV markers, UV illuminators, and cameras capable of capturing the UV spectrum. Athletes could be coated with sun block to reflect the UV light, which can be used to distinguish the athletes from the background. Normal television cameras can be fitted with UV filters to filter out any interference. The use of UV illuminators is not necessarily recommended due to the possibility that the illuminators may be hazardous to the health of the athletes and audience.

A thermal imaging camera can be used to detect the surface temperature changes of a boxer. The thermal camera can be used to both track the surface temperature of an athlete and as a way to distinguish between the athletes and other objects. Points of an athlete, identified by temperature, can be marked by a computer and followed throughout an event.

Data from cameras can be analyzed by connecting the cameras to an analysis system. A computer can analyze camera data to detect punch types. From above, punches can be seen in two dimensions, the x-axis and y-axis. Other cameras can be set on the sides of an event to give an x-axis and z-axis view, and a y-axis and z-axis view. The computer can mark identifiable portions of a boxer's body by differentiating those portions from background objects. Portions that can be marked include a boxing glove and a boxer's elbow. Once portions of a boxer's body are marked, discrete data can be generated from video captured by the cameras. The generated data can be analyzed to determine the type of punch thrown. Similar methods to analyzing acceleration data can be used on the video data. For example, from above, a left hook can be analyzed as an outward forward motion followed by an inward forward motion. A high resolution camera can even record the twisting of the forearm during a punch. From the point of view of a camera, a jab goes from a roughly vertical orientation while in guard position, quickly moves straight out from the leading shoulder and rotates approximately 90 degrees to finish with the palm facing downward at the end of the punch. The camera can isolate that movement using markers. Data could be correlated with data from an accelerometer and gyroscope to increase the reliability of the analysis.

Data from cameras can also be analyzed to determine uppercuts, left and right hooks, and other punches. A left hook can be seen by a camera connected to a computer as moving outward from the side of a boxer and then moving forward, with little vertical movement. An uppercut can be seen by the computer as having a good amount of vertical movement by the glove, with little horizontal movement. Once again, this data can be correlated with data from accelerometer, gyroscope, and impact sensors to increase the reliability of the analysis.

In yet another embodiment, the system can have a camera pointing at the triangulated position of the boxers for automatic camera movement. A computer can be programmed to create a three-dimensional grid of the boxing ring. The computer can then triangulate the positions of the boxers using distance information from multiple radios placed on each boxer. The camera can be equipped to be moved autonomously or semi-autonomously by computer. The computer can track the movements of the boxers in three dimensions through triangulation and signal the camera to move.

Once a camera detects the gloves, the body, and the heads of two boxers, a computer can determine where a punch hits with some accuracy. Multiple cameras can be used to capture data from multiple angles. The head of each boxer can be marked by the computer, along with the torso and boxing gloves. When a boxer's punch is thrown, the computer can analyze the glove's location compared to the head and body of the opponent. Camera data can be correlated with accelerometer and gyroscope data to coordinate when a punch is thrown, its impact, and its location. For example, a punch event can be recognized using accelerometer data. The type of punch can be deduced by comparing accelerometer and gyroscope data to motion profile rules. An impact time can be calculated using deceleration rules or an impact sensor. A camera can determine where the punch glove was as compared to the other boxer at the time of impact.

In another embodiment, the system can be used for training. The system can obtain raw data and analyze it while an athlete is training. Analysis software can display faults of an athlete's movements while training. For instance, if an amateur boxer is sparring with a professional boxer, both using a system to monitor their movements, the amateur boxer can compare the way he holds his hands as compared to the professional in order to improve in the future. The computer can even give the trainee instructions on how to improve. A trainee can also use the information to improve the force of his punch. Further, for training, additional sensors can be used that would normally not be used in a live event, such as piezoelectric sensors to sense force and heart rate monitors.

Though many of the embodiments discussed are examples of boxing, the systems and methods described can be applied to various physical environments. For instance, martial arts and other physical activities can use this technology for training, keeping statistics, scoring, and adding entertainment value. In one example, sensors can be placed in footwear for kickboxing and soccer. In another example, motion profiling techniques can be used to determine what motions occurred by using motion rules and profiles. Outcomes can be determined for a variety of motions and movements for different activities. Event data can be triggered by different thresholds to correspond with different sports. In ice skating, an event can begin when a certain threshold angular acceleration is begun. For example, an event can be started for calculating the rotational speed of a lutz and other jumps. In wrestling, moves, such as a suplex, body slam, or a chop, can be determined outcomes from data gathered through data capture devices. Other uses can include, without limitation, kicking a ball in soccer or football, gymnastics judging, free style skiing judging, diving judging, and the swinging of a golf club. Additionally, an outcome can be a foul or misstep, such as a step outside of a boundary or a punch below belt. Such outcomes can be used in judging to penalize an athlete or reduce an athlete's point total.

The above-described technology can be implemented on known devices such as a personal computer, a special purpose computer, cellular telephone, personal digital assistant (PDA), a programmed microprocessor or microcontroller and peripheral integrated circuit element(s), and ASIC or other integrated circuit, a digital signal processor, a hard-wired electronic or logic circuit such as a discrete element circuit, a programmable logic device such as a PLD, PLA, FPGA, PAL, or the like. In general, any device capable of implementing the processes described herein can be used to implement the systems and techniques according to this invention.

It is to be appreciated that the various components of the technology can be located at distant portions of a distributed network and/or the Internet, or within a dedicated secure, unsecured and/or encrypted system. Thus, it should be appreciated that the components of the system can be combined into one or more devices or co-located on a particular node of a distributed network, such as a telecommunications network.

Furthermore, it should be appreciated that the various links connecting the elements can be wired or wireless links, or any combination thereof, or any other known or later developed element(s) that is capable of supplying and/or communicating data to and from the connected elements. Programmable code can be embodied in a module including hardware, software, firmware, or combination thereof that is capable of performing the functionality associated with that code. The terms determine, calculate and compute, and variations thereof, as used herein are used interchangeably and include any type of methodology, process, mathematical operation or technique.

Moreover, the disclosed methods may be readily implemented in software, e.g., as a computer program product, executed on a programmed general purpose computer, cellular telephone, PDA, a special purpose computer, a microprocessor, or the like. In these instances, the systems and methods of this invention can be implemented as a program embedded on a personal computer such as a JAVA®, CGI or Perl script, as a resource residing on a server or graphics workstation, as a routine embedded in a dedicated image system, or the like. The systems and methods of this invention can also be implemented by physically incorporating this system and method into a software and/or hardware system, such as the hardware and software systems of a computer. Such computer program products and systems can be distributed and employ a client-server architecture.

The embodiments described above are intended to be exemplary. One skilled in the art recognizes that numerous alternative components and embodiments may be substituted for the particular examples described herein and still fall within the scope of the invention.

What is claimed is:

1. A computer-implemented method for analyzing activity of a boxer to permit assessments of that activity using a processor, the method comprising:
    receiving, by the processor, a stream of continuous activity-related data transmitted from a dual-axis accelerometer on the boxer, wherein the activity-related data includes acceleration data along each of the two axes representing a motion of the boxer;
    identifying, by the processor, a punch event within the stream of continuous activity-related data;
    analyzing, by the processor, the received activity-related data along both axes to determine whether the motion of the boxer represented by the activity-related data along both axes exceeds a threshold value;
    when the received activity-related data exceeds the threshold value, identifying, by the processor, the activity-related data as the punch event;
    storing, by the processor, the activity-related data of the punch event in a database;
    determining, by the processor, a time of impact of the punch event;
    extracting, by the processor, activity-related data before the punch event, including activity-related data below the threshold value;
    determining, by the processor, a starting time of the punch event;
    calculating, by the processor, a speed of the punch event based upon an integral of the acceleration data from the starting time of the punch event to the time of impact for the punch event;
    generating, by the processor, a motion profile of the punch event; and
    displaying the calculated speed of the punch event.

2. A computer program product comprising:
    a non-transitory computer usable medium having computer readable program code embodied therein for analyzing hand activity of a boxer having an accelerometer disposed on a hand of the boxer, the computer readable program code in the computer program product comprising:
    computer-readable program code for receiving a stream of continuous activity-related data transmitted from a dual-axis accelerometer on the boxer, wherein the activity-related data includes acceleration data along each of the two axes representing a motion of the boxer;
    computer-readable program code for identifying a punch event within the stream of continuous activity-related data;
    computer-readable program code for analyzing the received activity-related data along both axes to determine whether the motion of the boxer represented by the activity-related data along both axes exceeds a threshold value;
    computer-readable program code for when the received activity-related data exceeds the threshold value, identifying the activity-related data as the punch event;
    computer-readable program code for storing the activity-related data of the punch event in a database;

computer-readable program code for determining a time of impact of the punch event;

computer-readable program code for extracting activity-related data before the punch event, including activity-related data below the threshold value;

computer-readable program code for determining a starting time of the punch event;

computer-readable program code for calculating a speed of the punch event based upon an integral of the acceleration data from the starting time of the punch event to the time of impact for the punch event;

computer-readable program code for generating a motion profile of the punch event; and computer-readable program code for displaying the calculated speed of the punch event.

3. A computer-implemented method comprising:

receiving, by a computer from an accelerometer, a stream of continuous activity-related data transmitted from the accelerometer on a boxer, wherein the activity-related data includes acceleration data representing the motion of the boxer;

identifying, by the computer, a punch event within the stream of continuous activity-related data;

determining, by the computer, a type of punch in the punch event by comparing the activity related data to a motion profile;

determining, by the computer, a time of impact of the punch event;

calculating, by the computer, a speed of the punch event based upon an integral of the acceleration data from the starting time of the punch event to the time of impact of the punch event;

calculating, by the processor, a force of the punch event based upon the acceleration data of the punch event; and displaying, by the computer, the type of punch, the speed and the force of the punch event.

4. The method of claim 3, wherein the accelerometer is placed on the wrist of the boxer.

5. The method of claim 3, wherein the accelerometer is inserted into a pocket of the glove on the boxer.

6. The method of claim 3, further calculating based on the accelerometer data: punch counts, speed of the punch, force of the punch, and type of punch.

7. The method of claim 6, wherein type of punch comprises one or more of: a jab, a straight, a hook, and an uppercut.

8. The method of claim 3, further comprising: based on analysis of the boxer, providing options to chat or purchase merchandise.

9. The method of claim 3, further determining faults of the boxer's movement based on the activity related data.

10. The method of claim 3, further calculating a comparison between the boxer's form and a professional boxer's form.

11. A system comprising:

one or more computer processors;

a memory containing a program which, when executed by the one or more computer processors, is configured to perform an operation comprising:

receiving, by a computer from an accelerometer, a stream of continuous activity-related data transmitted from the accelerometer on a boxer, wherein the activity-related data includes acceleration data representing the motion of the boxer;

identifying, by the computer, a punch event within the stream of continuous activity-related data;

determining, by the computer, a type of punch in the punch event by comparing the activity related data to a motion profile;

determining, by the computer, a time of impact of the punch event;

calculating, by the computer, a speed of the punch event based upon an integral of the acceleration data from the starting time of the punch event to the time of impact of the punch event;

calculating, by the processor, a force of the punch event based upon the acceleration data and of the punch event; and displaying, by the computer, the type of punch, the speed and the force of the punch event.

12. The system of claim 11, wherein the accelerometer is placed on the wrist of the boxer.

13. The system of claim 11, wherein the accelerometer is inserted into a pocket of the glove on the boxer.

14. The system of claim 11, further calculating based on the accelerometer data: punch counts, speed of the punch, force of the punch, and type of punch.

15. The system of claim 14, wherein type of punch comprises one or more of: a jab, a straight, a hook, and an uppercut.

16. The system of claim 11, further comprising: based on analysis of the boxer, providing options to chat or purchase merchandise.

17. The system of claim 11, further determining faults of the boxer's movement based on the activity related data.

18. The system of claim 11, further calculating a comparison between the boxer's form and a professional boxer's form.

* * * * *